(12) United States Patent
Novikov (10) Patent No.: US 7,253,896 B1
(45) Date of Patent: Aug. 7, 2007

(54) FILTER

(75) Inventor: Valerie Alexey Novikov, deceased, late of St. Petersburg (RU); by Natalia Novikov, legal representative, St. Petersburg (RU)

(73) Assignee: BAH Holdings LLC, Massapequa, NY (US)

( * ) Notice: Subject to any disclaimer, the term of this patent is extended or adjusted under 35 U.S.C. 154(b) by 573 days.

(21) Appl. No.: 10/148,787

(22) PCT Filed: Nov. 28, 2000
(Under 37 CFR 1.47)

(86) PCT No.: PCT/GB00/04523
§ 371 (c)(1),
(2), (4) Date: Sep. 22, 2003

(87) PCT Pub. No.: WO01/40748
PCT Pub. Date: Jun. 7, 2001

(30) Foreign Application Priority Data

Dec. 2, 1999 (RU) .................................. 99125835

(51) Int. Cl.
*G01J 3/28* (2006.01)
(52) U.S. Cl. ....................................................... 356/327
(58) Field of Classification Search .................... None
See application file for complete search history.

(56) References Cited

U.S. PATENT DOCUMENTS

| | | | |
|---|---|---|---|
| 4,320,973 A | 3/1982 | Fortunato et al. | |
| 4,602,342 A | 7/1986 | Gottlieb et al. | |
| 4,652,756 A | 3/1987 | Ryan et al. | |
| 4,653,869 A | 3/1987 | Gottlieb et al. | |
| 4,663,961 A | 5/1987 | Nelson et al. | |
| 4,732,480 A | 3/1988 | Fortunato et al. | |
| 5,076,699 A | 12/1991 | Ryan et al. | |
| 5,694,205 A * | 12/1997 | Gualtieri et al. | 356/33 |
| 5,696,586 A | 12/1997 | Ivanov | |

FOREIGN PATENT DOCUMENTS

| | | |
|---|---|---|
| EP | 0395213 | 3/1990 |
| EP | 0396319 | 7/1990 |
| WO | PCT/GB/04523 | 2/2001 |
| WO | PCT/GB/04523 | 3/2002 |

\* cited by examiner

*Primary Examiner*—Tu T. Nguyen
(74) *Attorney, Agent, or Firm*—James B. Conte; Barnes & Thornburg LLP (57) ABSTRACT

A filter for use in a spectrometer to filter transmitted radiation and wherein the filter has a birefringent element responsive to an applied signal, a first polarizer for polarizing the radiation transmitted by a sample, a second polarizer for polarizing the radiation transmitted by the birefringent element, and wherein the birefringent element has a birefringent member having a first birefringence and the birefringent member being responsive to a force applied thereto to generate an additional second birefringence; and the filter having a driver for applying a force to the birefringent member in accordance with the applied signal, and the driver has a piezoelectric member coupled to the birefringent member on one end or at two opposite ends.

5 Claims, 11 Drawing Sheets

{C=Optical axis}

FILTER

Foreign priority, is claimed from Russian Federation Application 99125835, filed Dec. 2, 1999. This application is a 371 of PCT/GB00/04523, filed Nov. 28, 2000.

The present invention relates to filter for use in a spectrometer, and in particular a correlation interference polarization spectrometer (CIPS), for optically detecting gases.

BACKGROUND OF THE INVENTION

Optical methods for the detection of gases are based on the measurement of the absorption of incident radiation by the gas molecules. For any given wavelength of incident radiation, the quantity that is absorbed is a function of the "cross section" $\sigma(\lambda)$ ($cm^2$) of any particular molecule in the gas (i.e. the amount of absorption depends on the wavelength). If the dependence of the cross section on the wavelength is very pronounced, then the gas molecules will absorb radiation over a very narrow waveband. In this case the spectral displacement between the maximum and minimum intensities of the transmitted radiation is very small. By measuring the difference between the maximum and minimum intensity of the transmitted radiation it is possible to calculate the concentration of the gas.

Figure 1:
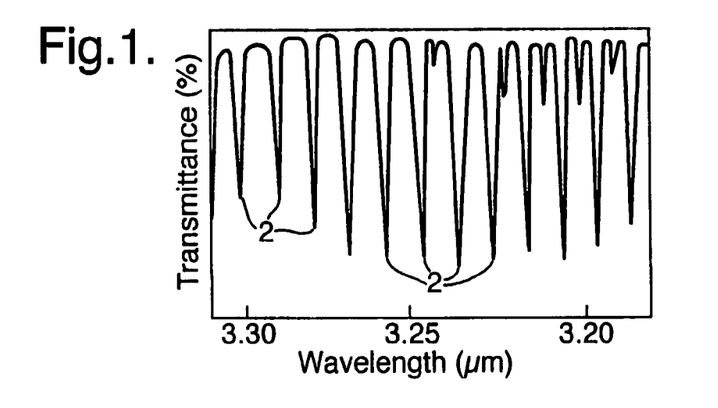
FIG. 1 is a view of the graph of the absorption spectrum of methane.

In the case of a CIPS, this uses the quasi periodical structure of the electronic absorption spectrum of the gas molecules, which is due to their vibrational-rotational properties. An example of such an absorption spectrum is provided in FIG. 1 which shows the absorption spectrum of methane, in the vicinity of 3.25 micrometers. This vibration-rotation spectrum consists of a number of very narrow (approximately 1 nm wide) quasi periodic absorption bands 2 that are detected by the CIPS.

This quasi periodic structure depends on the vibration and rotation of the gas molecules, and accordingly, this form of spectra is highly resolved such that the quasi periodic structure of the gas molecules absorption is well defined.

However, because of the manner in which the CIPS operates, which will be explained in more detail below, if the individual absorption lines of the quasi periodic absorption spectrum are not symmetrical then the signals detected by the CIPS will be modulated by this spectral asymmetry. Modulation will also occur if the sensitivity of the detector used in the CIPS varies monotonically with wavelength. This undesirable modulation can lead to problems in processing the results and therefore hinders the detection of gases.

BRIEF SUMMARY OF THE INVENTION

In accordance with a first aspect of the present invention, we provide a controlled interference polarization spectrometer for determining the concentration of a predetermined substance within a sample, the spectrometer comprising:

a radiation source for supplying radiation to the sample to be measured, separate, substantially similar portions of radiation output from the sample being fed to respective first and second filters.

the first filter having a number of pass bands at wavelengths corresponding to absorption peaks in the absorption spectrum of the substance to be detected, the first filter being responsive to an applied signal to modulate the wavelengths of the pass bands in a first direction, and the second filter having a number of pass bands at wavelengths corresponding to absorption peaks in the absorption spectrum of the substance to be detected, the second filter being responsive to an applied signal to modulate the wavelengths of the pass bands in a second direction opposite to the first direction; and, a detector for detecting the filtered radiation, the detector being responsive to the applied signal to determine the difference in the maximum and the minimum intensities of the radiation transmitted by the sample to thereby determine the concentration of the substance.

In accordance with a second aspect of the present invention, we provide a method of determining the concentration of a substance within a sample, the method comprising:

exposing the sample to radiation;

filtering a first portion of the radiation using a first filter having a number of pass bands at wavelengths corresponding to absorption peaks in the absorption spectrum of the substance to be detected, and modulating the wavelengths of the pass bands in a first direction; and, filtering a second portion of the radiation using a second filter having a number of pass bands at wavelengths corresponding to absorption peaks in the absorption spectrum of the substance to be detected, and modulating the wavelengths of the pass bands in a second direction opposite to the first direction; and, detecting the filtered radiation, the detection being performed in accordance with the modulation of the first and second filters to determine the difference in the maximum and the minimum intensities of the radiation transmitted by the sample to thereby determine the concentration of the substance.

Accordingly, the present invention provides a method and a CIPS for determining the concentration of a substance. This is achieved by filtering first and second portions of radiation transmitted by the substance to be detected. The filtering is performed by scanning the first and second portions of the radiation in opposite directions, and then superposing the filtered radiation. As a result, any asymmetries in the absorption spectra, or the wavelength dependence of the detector, are cancelled out. This has the advantage that during the analysis of an asymmetrical absorption spectra the maximum and minimum detected intensities remain constant as though the absorption spectra were symmetrical.

In this case the detector may comprise a detector element and a processor responsive to the detector element for generating an indication of the concentration of the substance. Alternatively, two detector elements may be used for detecting the first and second portions of the radiation respectively.

The spectrometer will also typically comprise a band filter positioned between the radiation source and the first and second filters, the band filter being arranged to transmit radiation having wavelengths in the region of the absorption spectrum of the substance to be detected. This advantageously reduces the amount of radiation incident on the first and second filters, thereby reducing the change of interference due to absorption to other wavelengths due to other substances. However, this may not be required if the detector only generates radiation over a limited wavelength range.

Preferably the method of determining the maximum and minimum intensities comprises:

determining the intensity of the detected radiation when the wavelengths of the pass bands are equal to the wavelengths of the absorption peaks for the first and second portions simultaneously; and, determining the intensity of the detected radiation when the wavelengths of the pass bands are between the wavelengths of the absorption peaks for the first and second portions simultaneously.

Alternatively, the detection may be carried out at different times, although in these circumstances, separate detector elements would need to be used to detect the first and second portions of the radiation independently.

In accordance with a third aspect of the present invention, we provide a filter for use in a spectrometer, the filter being arranged to filter radiation transmitted by a sample, the filter comprising:

a first polarizer for polarizing the radiation transmitted by the sample;

a birefringent element responsive to an applied signal, wherein the birefringent element modifies the polarization of the polarized radiation in accordance with the wavelength of the radiation and the applied signal; and, a second polarizer for polarizing the radiation transmitted by the birefringent element, the radiation being transmitted in a transmission direction, characterized in that the birefringent element comprises:

a first birefringent member having an optic axis arranged in a first direction perpendicular to the transmission direction, wherein the first birefringent member modifies the polarization of a first portion of the polarized radiation; and, a second birefringent member having an optic axis arranged in a second direction perpendicular to the transmission direction, the second direction being perpendicular to the first direction, wherein the second birefringent member modifies the polarization of a second portion of the polarized radiation.

Accordingly, the present invention also provides a filter which operates to filter first and second portions of the incident radiation differently. In this case the filter effectively defines two comb filters scanning in opposite directions which is ideal for use as the first and second filters of the first aspect of the invention.

However, it will be realised that the first and second aspects of the present invention can be implemented using any suitable filter system such as counter scanning comb filters defined by diffraction gratings or the like.

Typically the second portion is equal to the first portion, although any ratio may be used if the CIPS is configured accordingly.

Typically the birefringent element further comprises an optically isotropic member, the optically isotropic member being responsive to a force applied thereto to generate a birefringence; and, a driver for applying a force to the optically isotropic member in accordance with the applied signal. However, the force may be applied directly to the first and second birefringent members in order to generate an additional induced birefringence in the first and second birefringent crystals.

Preferably, the optically isotropic member is arranged to modify the polarization of the first and second portions of the polarized radiation. Alternatively, the optically isotropic member may only alter the polarization of one of the first and second portions, with a further optically isotropic member being used to alter the polarization of the other portion.

A further problem with a CIPS is that the filters typically require the use of two optical elements for providing a fixed birefringence and an additional modulated birefringence, respectively. This results in the filter system used being complicated as well as expensive to produce.

In accordance with a fourth aspect of the present invention, we provide a filter for use in a spectrometer, the filter being arranged to filter radiation transmitted by a sampled, the filter comprising:

a first polarizer for polarizing the radiation transmitted by the sample;

a birefringent element responsive to an applied signal, wherein the birefringent element modifies the polarization of the polarized radiation in accordance with the wavelength of the radiation and the applied signal; and, a second polarizer for polarizing the radiation transmitted by the birefringent element, the radiation being transmitted in a transmission direction, characterized in that the birefringent element comprises:

a birefringent member having a first birefringence, the birefringent member being responsive to a force applied thereto to generate an additional second birefringence; and, a driver for applying a force to the birefringent member in accordance with the applied signal.

The present invention therefore provides a filter having a single birefringent member that provides both the natural first birefringence and the induced second birefringence. This allows the filter to be implemented using only a single birefringent member whilst still allowing the scanning function of the filter to be achieved.

Typically the birefringent member comprises a single axis crystalline material. Suitable materials include Crystalline Silicon, Tellurium Dioxide, Islandic Spar or the like.

Preferably the driver comprises a piezoelectric member coupled to the birefringent member, although any suitable driver may be used. Thus, the driver could alternatively comprise a number of piezoelectric electrodes coupled to the surface of the birefringent member, the electrodes being arranged to generate a standing half-wave along the length of the birefringent member, in response to the applied signal.

Preferably, the birefringent member and the piezoelectric member are arranged such that the application of the signal to the piezoelectric member generates a standing wave along the combined length of the birefringent member and the piezoelectric member. This allows the magnitude of the induced birefringence to be accurately controlled, although any suitable method may be used.

The standing wave or standing half-wave is usually generated in a direction parallel to the direction of the optic axis of the birefringent member. However, the standing wave may also be generated in a direction perpendicular to the optic axis of the birefringent member.

A further problem with CIPS is that they utilize a number of polarizers in the filter system. Unfortunately, polarizers for polarizing infra-red radiation are typically very expensive. Accordingly, to produce a CIPS for detecting gases having an absorption spectrum in the IR wavelength is typically very expensive.

In accordance with a fifth aspect of the present invention, we provide a filter for use in a spectrometer, the filter being arranged to filter radiation transmitted by a sample, the filter comprising:

a first reflection polarizer for polarizing the radiation transmitted by the sample;

a birefringent element responsive to an applied signal, wherein the birefringent element modifies the polarization of the polarized radiation in accordance with the wavelength of the radiation and the applied signal; and, a second reflection polarizer for polarizing the radiation transmitted by the birefringent element.

Accordingly by using reflection polarizers, the use of transmission polarizers can be avoided.

Typically in this case, the system is either adapted to utilizes circular polarization of light, or alternatively the optic axis of the birefringent member is arranged at 45° to the vector of polarization of the radiation reflected from the first polarizer.

In accordance with a sixth aspect of the present invention, we provide a filter for use in a spectrometer, the filter being arranged to filter radiation transmitted by a sample, the filter comprising:

a first circular polarizer for polarizing the radiation transmitted by the sample;

a birefringent element responsive to an applied signal, wherein the birefringent element modifies the polarization of the polarized radiation in accordance with the wavelength of the radiation and the applied signal; and, a second circular polarizer for polarizing the radiation transmitted by the birefringent element.

Accordingly, the present invention also provides for using circular polarization within the filter system. This has the advantage that the optic axis of the birefringent member can be arranged at any angle as long as it is perpendicular to the direction of transmission of the radiation through the birefringent element. This helps reduce errors within configuring the apparatus that may occur if the birefringent element optic axis is to be arranged at a specific angle.

Furthermore, the first circular polariser typically comprises in order, a first linear polariser and a first quarter wave plate, and the second circular polariser typically comprises in order, a second quarter wave plate and a second linear polarizer.

This allows the linear polarizers to be formed from reflection polarizers which obviates the need for transmission polarizing elements. This further allows the invention to utilize cheaper elements whilst not requiring specific orientation of the birefringent element with respect to the linear polarizer.

Typically in the fifth and sixth aspect of the present invention, the birefringent element comprises a birefringent member having an optic axis arranged in a direction perpendicular to the transmission direction, wherein the birefringent member modifies the polarization of the radiation in accordance with the wavelength; and, an optically isotropic member the optically isotropic member being responsive to a force applied thereto to generate a birefringence; and, a driver for applying a force to the optically isotropic member in accordance with the applied signal. However, it will be realised that a single birefringent element which is responsive to an applied force to generate an additional birefringence, for example as used in the fourth aspect of the present invention, may be used.

The birefringent element used in the third, fourth, fifth or sixth aspects of the invention typically further comprises a temperature adjusting device for adjusting the temperature of the birefringent element to thereby adjust the birefringence of the birefringent element. This allows the exact birefringence of the birefringent element to be accurately controlled thereby producing the desired filtering.

The present invention also provides a controlled interference polarization spectrometer for determining the concentration of a substance within a sample, the spectrometer comprising a radiation source for supplying radiation to the sample to be measured; a band filter which allows only wavelengths in the vicinity of the desired absorption spectral to pass; a filter according to any of the third, fourth, fifth and sixth aspects of the present invention; and, a detector for detecting the filtered radiation, the detector being responsive to the applied signal to determine the difference in the maximum and the minimum intensities of the radiation transmitted by the sample to thereby determine the concentration of the substance.

BRIEF DESCRIPTION OF THE SEVERAL VIEWS OF THE DRAWINGS

Examples of the present invention will now be described with reference to the accompanying drawings, in which.

DETAILED DESCRIPTION OF THE INVENTION

Figure 2:
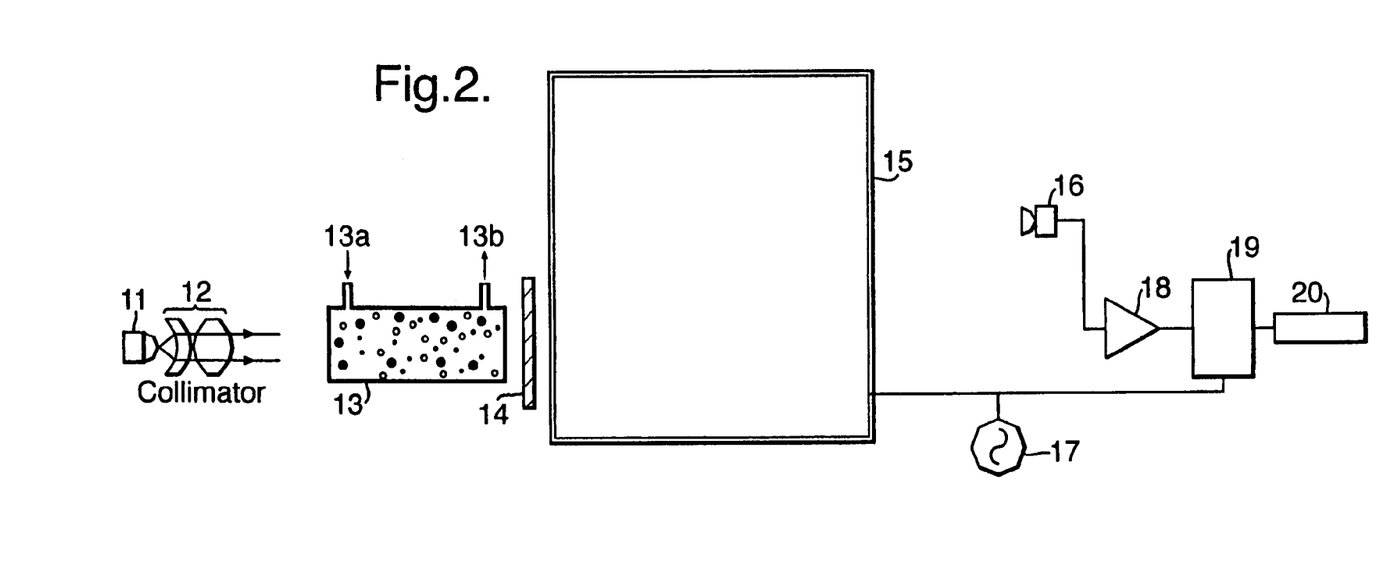
FIG. 2 is a schematic diagram of an example of CIPS apparatus.

An example of a CIPS adapted to detect the quasi periodic structure of the gas molecules absorption spectrum is shown in FIG. 2.

This type of spectrometer can be operated either as an active device using an emitter, such as an incandescent lamp or as a passive device, using the sun as an emitter. The design shown in FIG. 2 is for an active CIPS system.

The CIPS includes a radiation source 11 positioned next to a collimator 12. The collimator operates to convert the incident radiation into a co-linear beam which then passes through a gas cell 13. The gas cell contains the gas to be detected and includes an input aperture 13a and an output aperture 13b. Radiation transmitted through the gas cell 13 is then filtered using a narrow band filter 14 which allows only wavelengths in the vicinity of the desired absorption spectra to pass. Thus, for example, to detect methane then the bandpass filter would allow radiation in the 3.25 micrometer region to pass.

Following the filter 14 is a controlled interference polarization filter (cIPF) section 15. The cIPF 15 generates a transmission spectrum that consists of very narrow pass bands coinciding with the quasi periodic absorption spectrum of the target gas. The cIPF 15 is controlled to cause the transmission spectrum to be scanned back and forth within the selected working range. The operation of the cIPF 15 is controlled by an alternating voltage supply 17 which drives the cIPF and the detection system.

The detection system consists of a detector 16 coupled to an amplifier 18 which operates to amplify signals detected by the detector 16. The output of the amplifier 18 is coupled to a microprocessor 19 which is also coupled to the voltage supply 17 so as so synchronize the processing of the detected signal with the operation of the cIPF 15. Signals obtained from the microprocessor 19 are then output to a display 20 which displays an indication of the concentration of the detected gas.

The cIPF 15 is formed from a modified Interference Polarization Filter (IPF) which uses the phenomenon of birefringence in certain crystals to obtain a transmission spectrum which is characterized by a quasi periodic sequence of spectral pass bands.

Figure 3A:
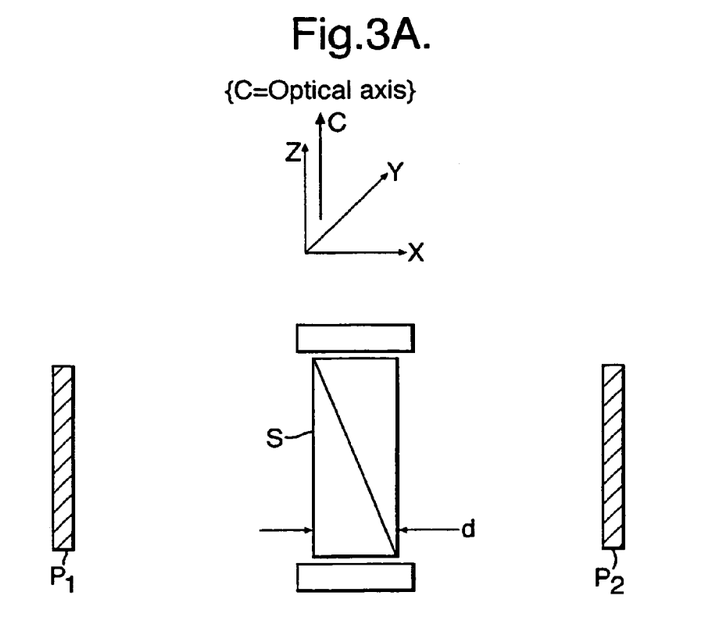
FIG. 3A is a schematic view of a single stage Woods filter.

Whilst any form of IPF, such as a SOLC or Lyot filter may be used, the present example will be described with reference to a simple prior art Woods filter which is shown in FIG. 3A. This includes input and output polarizers $P_1$, $P_2$ and an etalon formed from a birefringent crystal S.

The input polarizer $P_1$ converts the unpolarized incident radiation into a linearly polarized beam, in which the rays are polarized at 45° to the Z-axis in the Y-Z plane. The birefringent crystal S has its optical axis C aligned with the Z-axis so that the radiation is polarized at 45° with respect to the optical axis. Inside the birefringent crystal the linearly polarized beam splits into two beams having equal intensities but polarizations perpendicular to each other. These are referred to as the ordinary and extra-ordinary rays which travel through the crystal with velocities shown below:

$$v_o = c/n_o \text{ (ordinary ray)}$$

$$v_e = c/n_e \text{ (extra ordinary ray)}.$$

where: c—the speed of radiation in vacuum
$n_o$—refractive index for ordinary ray
$n_e$—refractive index for extra-ordinary ray As the two rays exit the crystal they interfere with each other. The result of this interference depends on the optical thickness of the crystal (d). Accordingly, the phase retardation δ between the two rays is given by $$\delta = 2\pi d(n_o - n_e)/\lambda$$

where λ—wavelength of radiation

The phase retardation is therefore a function of the wavelength. The state of polarization of the interfering rays will therefore be a periodic function of the wavelength as shown in FIG. 3B, which represents the amplitude against the wavelength (λ) for radiation transmitted by the Woods filter of FIG. 3A.

Thus, if the phase retardation is an even number of half wavelengths, the polarization of the exiting beam will be the same as that of the incident beam (i.e. plane polarized). Accordingly, the polarization vector of the radiation transmitted by the birefringent crystal S is aligned with the polarization vector of the output polarizer $P_2$ resulting in maximum transmission.

If the phase retardation is an odd multiple of half wavelengths the exiting beam will also be linearly polarized, with its plane of polarization making an angle of 90° with the plane of polarization of the incident beam. Accordingly, the polarization vector of the radiation is perpendicular to the polarization vector of the output polarizer $P_2$ resulting in minimum transmission.

Figure 3B:
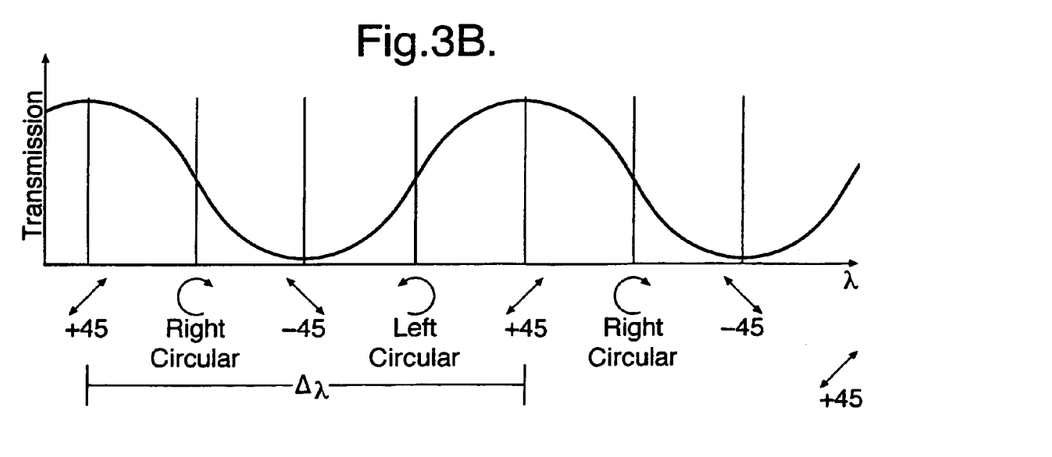
FIG. 3B shows the transmission spectrum for different wavelengths for the apparatus shown in FIG. 3A.

For all other values of the phase retardation the exiting beam will be generally elliptically polarized, resulting in partial transmission as shown in FIG. 3B.

The birefringent crystal S of an IPF can be either a traditional single axis crystal, such as quartz (having a birefringence index μ that varies from 0.01419 at λ=185 nm. to 0.0074 at λ=3 um.) or islandic spar (having a birfringence index μ that varies from 0.2028 at λ=312 nm. to 0.1606 at λ=1.23 um.) or a new type of crystal, such as paratelluride (having a birefringence index μ that varies from 0.185 at λ=0.4 um. to 0.14 at λ=4.7 um).

In order to be able to use the IPF in the detection of gases, the IPS must provide a transmission spectrum that closely matches the quasi periodic absorption spectra of the gas to be detected (i.e. the bandwidth between adjacent peaks in the absorption spectrum of the gas to be detected must correspond to the bandwidth between adjacent transmission peaks in the "IPF" transmission spectrum). Furthermore the IPF must be able to shift this spectrum in time, so that one can detect the magnitude both of the absorption (eg: $\lambda_2$=CH4) and non absorption (eg:$\lambda_1$=CH4) bands of the absorption spectrum of the target gas.

In order to achieve this, the IPFs are modulated by changing any of the following characteristics:
(1) change the width of the natural birefringent section;
(2) change the type of birefringent material used; or,
(3) introduce an additional birefringent section.

The spectral scanning of the radiation passing through an IPF can therefore be accomplished in a number of ways. For example, by mechanically rotating the output polarizer by 90°, with respect to the optical axis of the birefringent crystal. Alternatively nematic liquid crystals can be used together with an IPF to achieve tuneability.

Figure 4A:
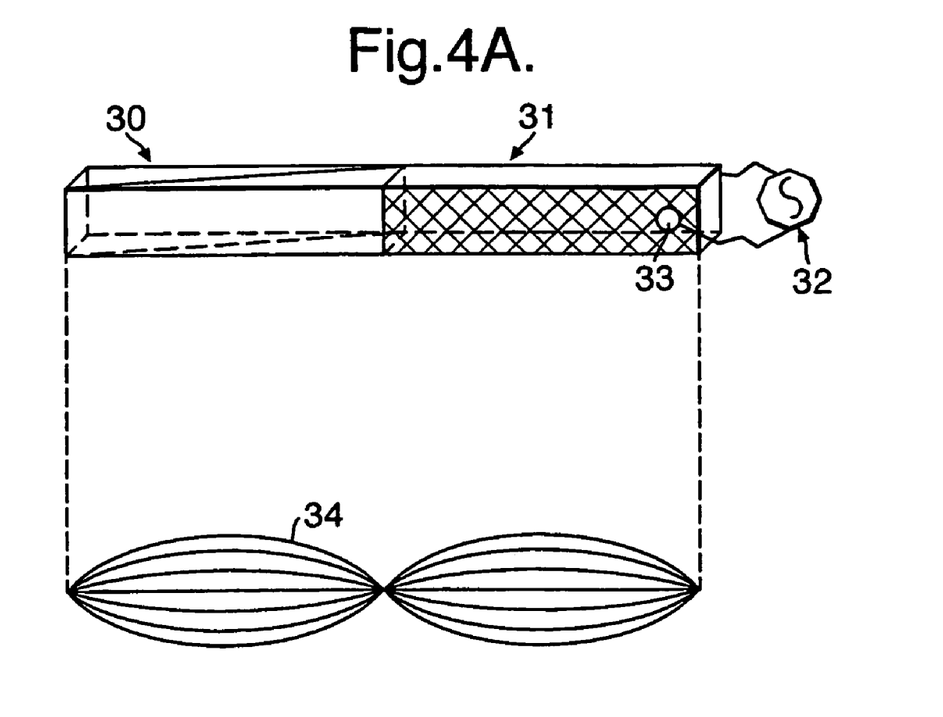
FIG. 4A shows an induced birefringent member for use in a Woods filter.

However, the most versatile method is the use of a Photoelastic Modulator of Polarization (PMP), an example of which is shown in FIG. 4A.

The photoelastic modulator includes an isotropic material 30 such as fused quartz that is being mechanically stressed using a piezoelectric driver element 31 and an alternating voltage source 32. The stress is arranged to be applied periodically along one of the edges of the isotropic material 30 so that the isotropic material 30 generates an induced birefringence that is periodic with time.

The difference in the induced refractive indexes ($n_o = n_e$) in the photo elastic modulator is proportional to the magnitude of the stress applied to the isotropic material 30 by the piezoelectric driver element 31. Accordingly, at any instant of time, the amplitude of the deformation determines the value of the induced birefringence, μ. As a result the spectral location of the transmission maxima of the filter's pass bands is varied by changing the stress applied to the crystal.

In the cIPF, the lengths of the isotropic material 30 and the piezoelectric driver element 31 are selected so that the self resonant frequencies of longitudinal vibrations are equal. The frequency of vibration is then selected to generate a single full standing wave for the entire system, as indicated by the standing wave 34. This results in a standing half-wave being generated in the isotropic material 30. This establishes a maximum mechanical stress and hence a maximum value for $(n_o - n_e)$ in the middle of the isotropic material 30. The magnitude of the applied stress and therefore the magnitude of the birefringence μ therefore depends on the amplitude of the voltage driving the piezoelectric driver element 31.

In the cIPF, the maximum stress and therefore maximum birefringence for the isotropic material 30, is set to correspond to a phase retardation exactly equal to λ/2 (i.e. half wave retardation).

In the example shown, a section of fused quartz acts as the isotropic material 30 and a section of piezoelectric quartz acts as the piezoelectric driver element 31. The piezoelectric driver element 31 is driven by two electrodes only one of which is shown as electrode 33.

Operation of the PMP in a simple Woods filter will now be described with reference to FIG. 4B.

Firstly, the isotropic material 30, the polarizers $P_1$, $P_2$ and the naturally birefringent crystal S are arranged as shown. In this case, a beam of radiation 35 incident on the polarizer $P_1$ as shown, passes through the middle of the isotropic material 30 as shown in FIG. 4C. In the undriven state the isotropic material 30 is not birefringent and therefore there are no changes in the passing beam and its spectral distribution.

The intensity of incident radiation 35 having a wavelength $\lambda_2$ coinciding with the λmax of the transmission of the IPF will be at the maximum and equal to Jo/2 (where Jo is the intensity of the radiation having a wavelength $\lambda_2$ incident on the input polarizer $P_1$). For these rays their polarization as they exit the IPF is linear and their polarization vector is aligned (parallel) to the polarization vector of the output polarizer $P_2$.

Meanwhile, radiation having a wavelength $\lambda_1$ corresponding to the $\lambda_{min}$ of the transmission of the IPF will have a minimum intensity equal to 0.

Figure 4B:
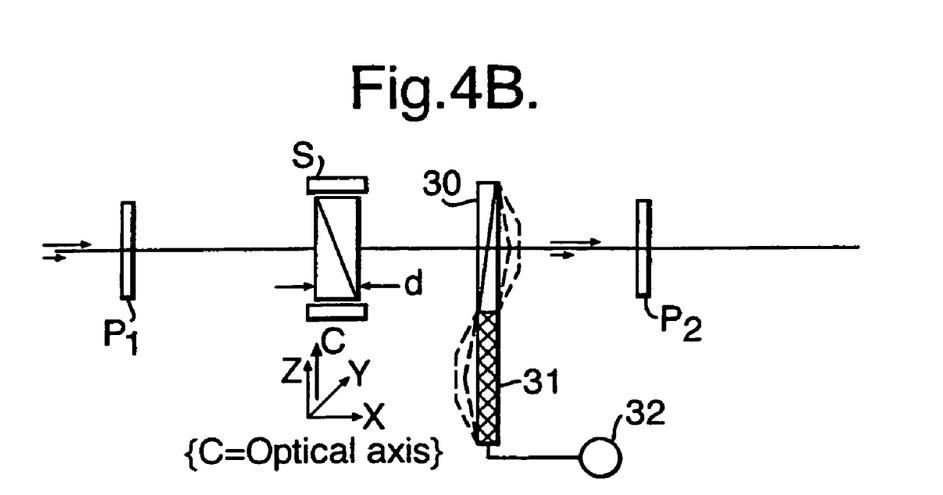
FIG. 4B is a schematic diagram of a prior art scanning Woods filter employing an induced birefringent member.
Figure 4C:
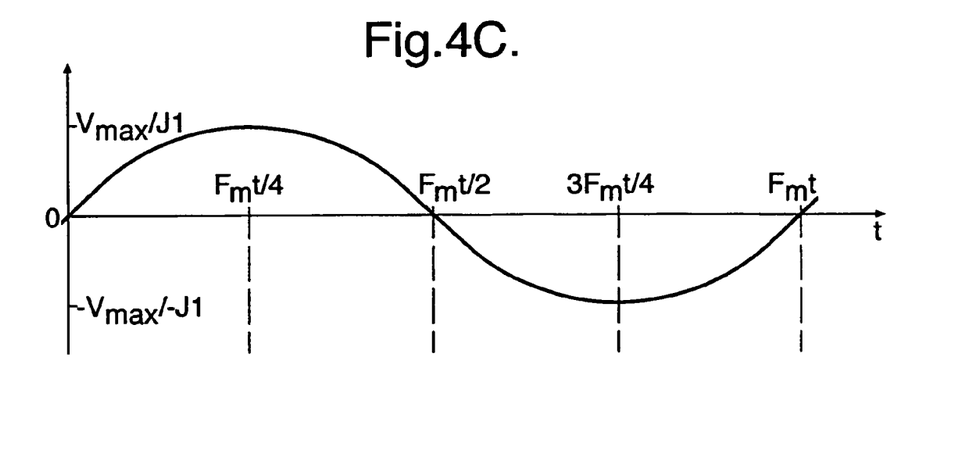
FIG. 4C shows the driver voltage applied to the apparatus of FIG. 4B against time with amplitude in which the induced birefringency is equal to half-wave phase plate or phase retardation II.
Figure 4D:
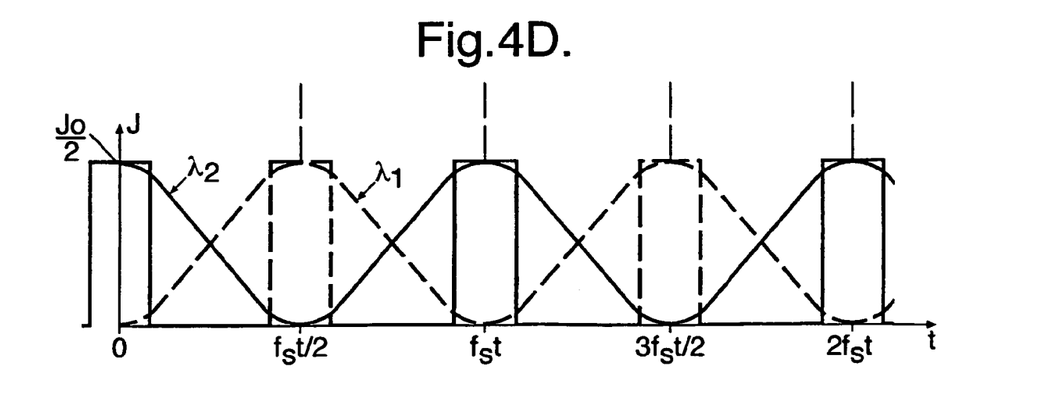
FIG 4D shows the transmission amplitude intensity against time for the apparatus shown in FIG. 4B and for the driver voltage shown in FIG. 4C.

This is shown in FIG. 4D, which is a graph of the intensity of the transmitted radiation 35, for the wavelengths $\lambda_2$, $\lambda_1$ against time t. The voltage and hence stress applied to the isotropic material 30 is shown in FIG. 4C, using a similar time scale. Thus, at t=0, the applied voltage is zero, the intensity of the radiation 35 having a wavelength $\lambda_2$ is Jo/2, and the intensity of radiation having a wavelength $\lambda_1$ is 0.

As the induced birefringence is increased with the applied excitation the polarization vector for the radiation having a wavelength $\lambda_2$ exiting the isotropic material 30 becomes first elliptical, then circular, then elliptical again and finally, when the phase retardation becomes δ=π, the exiting rays are again linearly polarized.

However, in this case the polarization vector is rotated by 90° with respect to the plane of polarization of the output polarizer $P_2$. Accordingly, the intensity of the radiation 35 exiting output polarizer $P_2$ and having a wavelength $\lambda_2$ reduces to a minimum.

As the birefringent crystal is driven sinusoidally with a frequency $F_m$, then the first minimum of transmission for the radiation 35 with the wavelength $\lambda_2$ will be at:

$$t=(F_m T/4)$$

Thus, at time intervals corresponding to $2n(F_m t/4)$ the output for the radiation 35 with the wavelength $\lambda_2$ will be a maximum whilst the radiation 35 having a wavelength $\lambda_2$ the intensity will be 0, as shown in FIG. 4D.

Maximum transmission for the wavelength $\lambda_2$ occurs when the phase retardation becomes δ=π. Hence, for a time period corresponding to one full cycle of the driving frequency there will be two maxima and two minima outputs for the radiation having a wavelength $\lambda_2$. A similar situation exists for radiation having a wavelength $\lambda_1$ as shown.

Accordingly the frequency of change of the luminous flux (fs) is twice the selected modulation frequency of the crystal $fs=2F_m$.

Figure 4E:
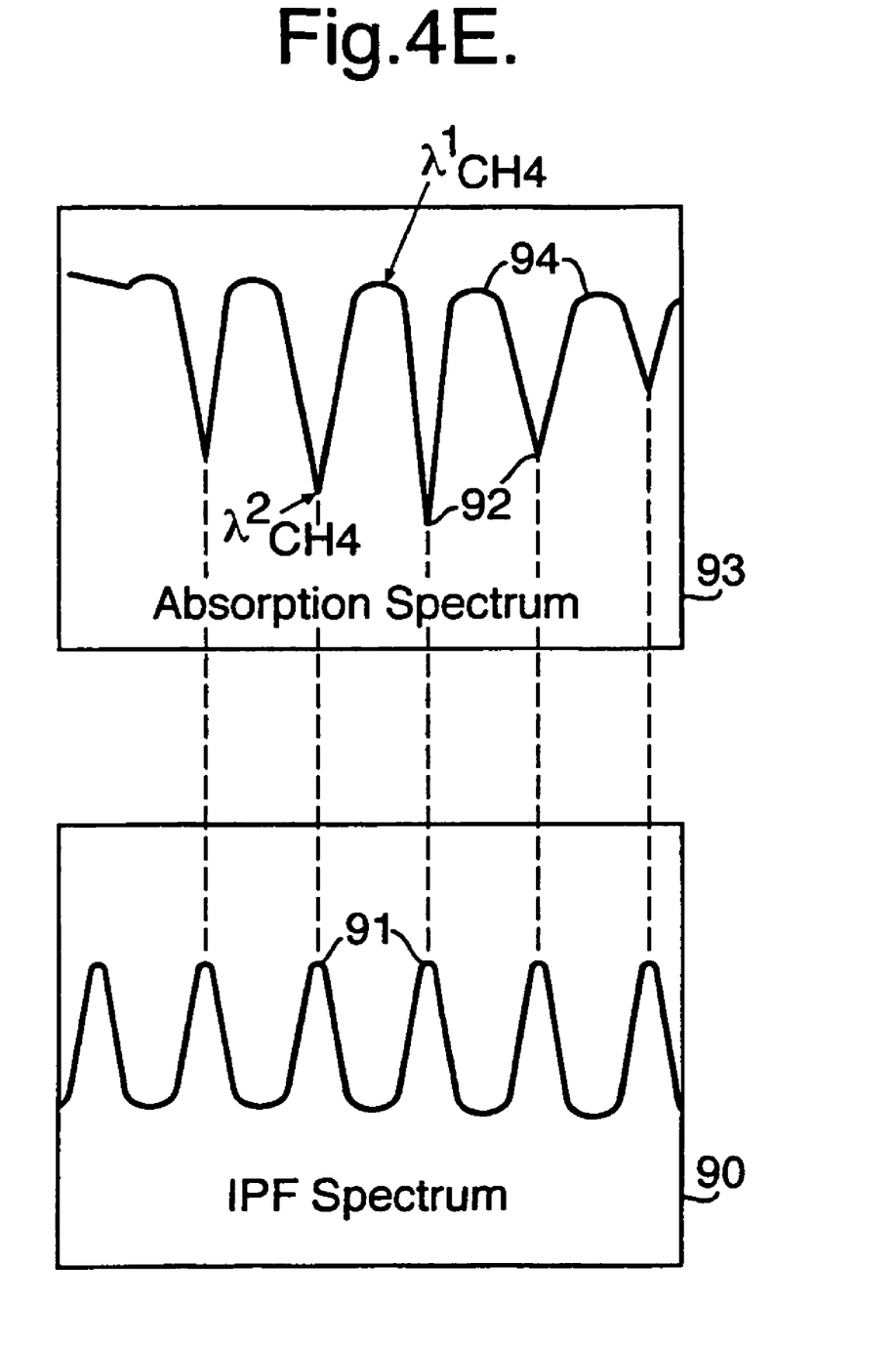
FIG. 4E is an example of the transmission spectrum of the apparatus of FIG. 4B, compared to the absorption spectrum of methane.

An example of the transmission spectrum of the cIPF is shown at 90 in FIG. 4E. The wavelength dependency of the birefringent effect means that the transmission spectrum of the cIPF includes a number of transmission peaks 91 (i.e. the cIPF acts as a comb filter). By choosing an appropriate birefringent crystal S, the transmission peaks 91 can be selected to correspond to absorption peaks 92 in the vibrational-rotational spectrum of the target gas which is shown at 93.

Accordingly, with the peaks 91,92 aligned as shown, the radiation transmitted by the cIPF will be the radiation having wavelengths which are absorbed by the target gas.

Furthermore, as a stress is applied to the isotropic material 30, the combined birefringence of the crystal S and the isotropic material 30 alters, causing the transmission spectrum of the cIPF to alter. Accordingly, the comb filter effectively scans from left-to-right and then back again.

When the transmission peaks 91 are aligned with troughs 94 in the vibrational-rotational spectrum 93, then the radiation transmitted by the cIPF represents wavelengths which are transmitted by the target gas. This allows the maximum and minimum transmission intensities in the absorption spectrum of the gas to be determined (i.e. the height of the peaks can be determined).

Thus, by choosing an appropriate amplitude driving signal, the cIPF can act as a modulator, scanning the vibrational-rotational spectrum of the sample gas from one maxima, to the next and back again. This makes the cIPF of FIG. 4B ideal for use in the apparatus of FIG. 2.

Figure 5:
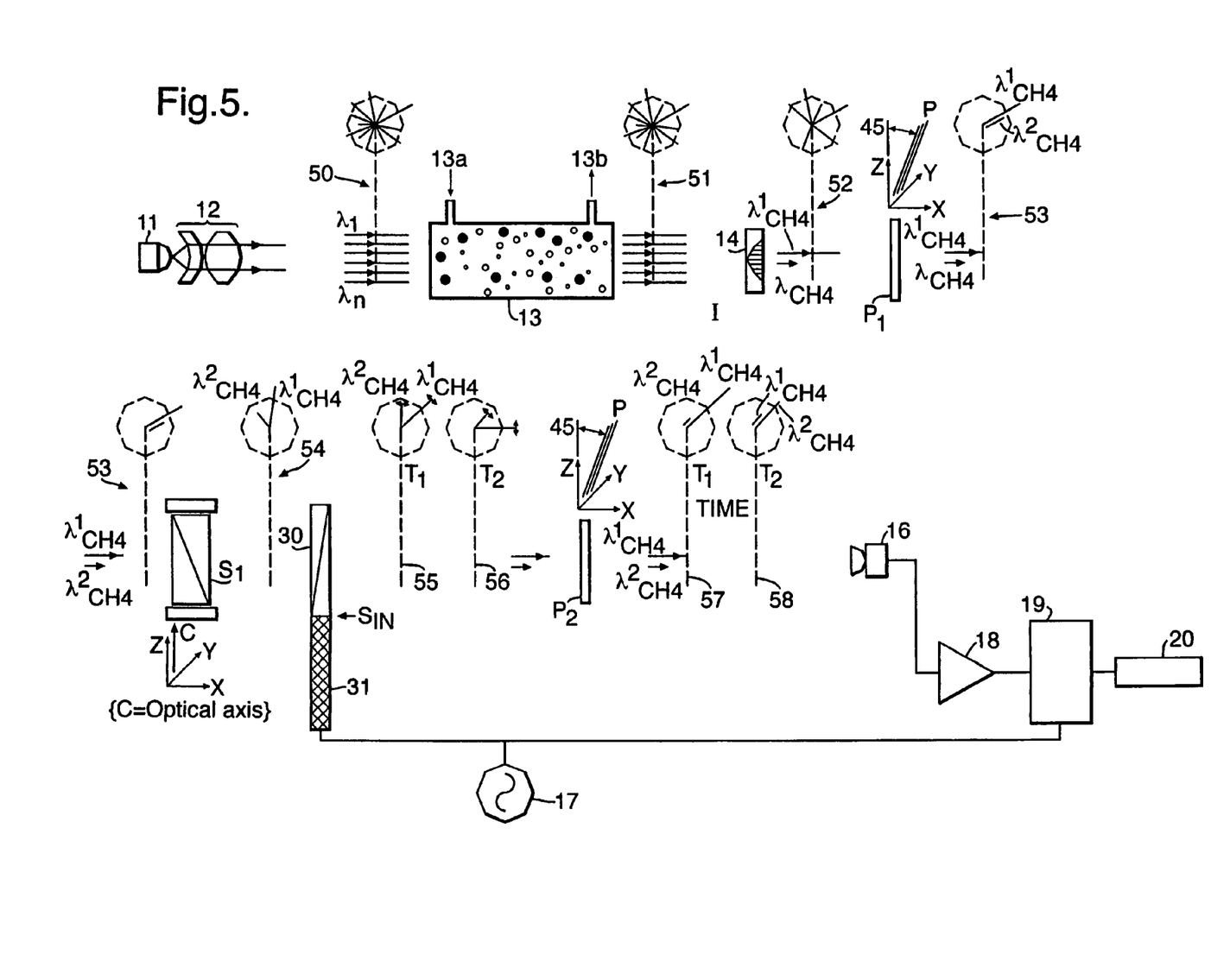
FIG. 5 is a schematic diagram of a prior art CIPS which uses the filter of FIG. 4B.

Thus a CIPS using a cIPF according to the prior art is shown in FIG. 5.

In this case, the CIPS has a cIPF 15 having an input polarizer $P_1$, a birefringent crystal S, and an induced birefringent member $S_{in}$ and an output polarizer $P_2$. The induced birefringent member $S_{in}$ includes the isotropic material 30, and the piezoelectric driver element 31. In this case the voltage source 32 is replaced with the voltage source 17, as shown.

FIG. 5 also includes representations of the radiation 50,51,52,53,54,55,56,57,58 as it passes through the apparatus at the respective location. In the representations, radial distance from the centre point represents the radiation amplitude, whilst the angular position represents the polarization.

Operation of the apparatus shown in FIG. 5 will now be described. Firstly, radiation emitted by the source 11 is transmitted through the collimator to form a collimated beam of radiation 50. As shown in representation, this collimated beam of radiation includes a selection of different wavelengths of radiation which are randomly polarized.

The collimated radiation 50 is transmitted through the gas cell 13 which causes the absorption of the radiation in the wavelengths corresponding to the absorption spectrum of methane. In this example the wavelengths are indicated as $\lambda^2_{CH4}$ for wavelengths having the maximum absorption (and therefore minimum transmission) and $\lambda^1_{CH4}$ for wavelengths having a minimum absorption. Accordingly, the radiation 51 output from the gas cell 13 will include a deficiency in the wavelengths $\lambda^1_{CH4}, \lambda^2_{CH4}$.

The transmitted radiation 51 is then bandpassed by the band filter 14. This is done such that the filtered radiation 52 includes only wavelengths in the region of the methane absorption spectrum.

The radiation 52 then enters the cIPS 15 which filters the radiation as described above with respect to FIG. 4D. Thus the polarized radiation 53 is transmitted by the birefringent crystal S which rotates the plane of polarization so that the radiation 54 includes each wavelength $\lambda^1_{CH4}, \lambda^2_{CH4}$ rotated by a different amount.

The radiation 54 is transmitted by the isotropic material 30 of the induced birefringent member $S_{in}$ which is driven at a frequency depending on the structure of the modulator. This causes the polarization of the wavelengths $\lambda^1_{CH4}, \lambda^2_{CH4}$ to rotate over time. Thus at time $t=T_1$, the radiation 55 has different polarizations to the radiation 56 at time $t=T_2$, as shown.

The radiation 55,56 is polarized by the polarizer $P_2$ which again acts to allow radiation polarized at 45° to the Z axis, in the Y,Z plane, to be transmitted. The output radiation 57,58 therefore includes different proportions of the wavelengths $\lambda^1_{CH4}, \lambda^2_{CH4}$ depending on the birefringence induced in the induced birefringent member $S_{in}$.

In this example the birefringent crystal S is selected so that the wavelengths from the absorption spectrum of the gas $\lambda^1_{CH4}$ and $\lambda^2_{CH4}$ correspond to the wavelengths $\lambda_1$ and $\lambda_2$ used in the explanation of FIG. 4D.

Thus, at time $t=0$ when the transmission peaks 91 of the transmission spectrum 90 of the CIPF 15 correspond to the absorption peaks 92 of the absorption spectrum of the gas 93, then there will be maximum transmission of wavelengths having a wavelength $\lambda^2_{CH4}$, correspond to $\lambda_2$ in FIG. 4D. Thus, the intensity of radiation having a wavelength $\lambda^2_{CH4}$ will be $J_o/2$ (i.e. Half the intensity of the radiation 52 having a wavelength $\lambda^2_{CH4}$ which is incident on the polarizer $P_1$).

At the same time the transmission intensity of radiation having a wavelength $\lambda^1_{CH4}$ will be 0. Accordingly, the detector will detect a signal representative of the intensity of the radiation $\lambda^2_{CH4}$ which has been transmitted by the gas.

At time $$T = f_s T/2$$

the situation is reversed and the transmission peaks 91 of the transmission spectrum 90 of the CIPF 15 correspond to the troughs 94 in the absorption spectrum. Accordingly, only radiation having a wavelength $\lambda^1_{CH4}$ will be transmitted by the CIPF 15. The detector will therefore detect only radiation of this wavelength.

The detector transfers a signal representative of the intensity of received radiation to the processor 19. The processor 19 is coupled to the voltage generator 17 and uses a signal to monitor the output from the detector at time $$T = NF_m T/4$$

Accordingly, the processor 19 will obtain an indication of the intensity of the wavelength $\lambda^2_{CH4}$ at $T=0, F_m T/2$, $F_M T, \ldots$. The processor 19 will also obtain an indication of the intensity of the wavelength $\lambda^1_{CH4}$ at times $T=F_m T/4$, $3F_m T/4, \ldots$.

This allows the processor 19 to determine the difference in intensities between the peaks 92 and the troughs 94, thereby allowing the concentration of the selected gas in the sample to be calculated.

Figure 6A:
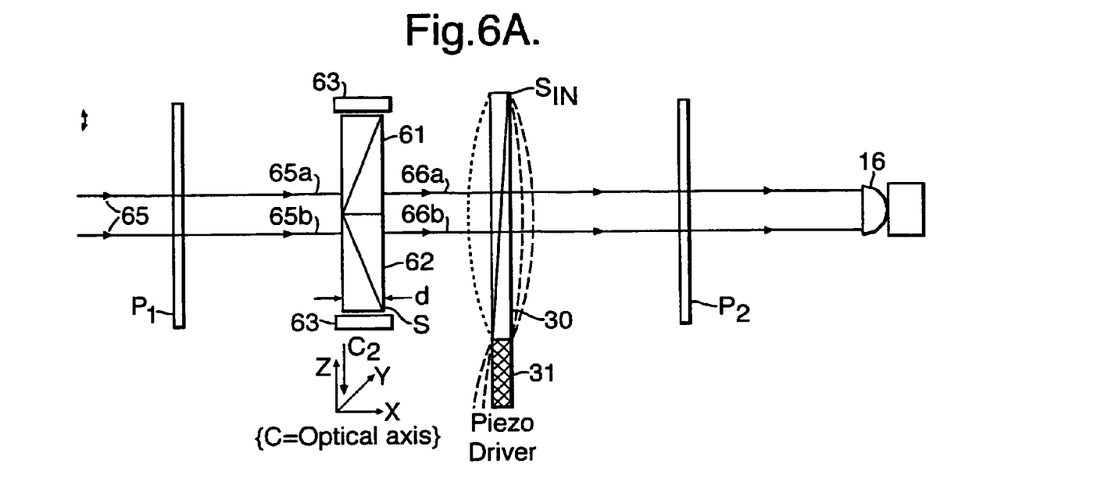
FIG. 6A is a schematic diagram of apparatus according to a first aspect of the present invention.

The apparatus shown in FIG. 6A is an example of a cIPF according to the first aspect of the present invention. In this case the cIPF 15 includes an input polarizer $P_1$ an output polarizer $P_2$, an induced birefringent member $S_{in}$ and a naturally birefringent element S.

The naturally birefringent element S includes first and second crystals 61,62 positioned adjacent each other, as shown. The first crystal 61 has its optical axis $C_1$ arranged parallel to the Y axis, whereas the second crystal 62 has its optical axis $C_2$ arranged parallel to the Z axis, as shown. The radiation input into the cIPF is shown generally by the rays 65.

The cIPF also includes temperature adjustment means, such as heating and/or cooling elements 63 which operate to maintain the first and second crystals 61,62 at a constant temperature.

Operation of the cIPF of FIG. 6A will now be described. Firstly, the radiation 65 is polarized by the polarizer $P_1$, in the normal way. The polarized radiation is then incident on the first and second crystals 61,62 in equal proportions represented by the rays 65A, 65B as shown.

For the radiation 65B incident on the second crystal 62, the optical axis $C_2$ is arranged parallel to the Z axis, and the birefringence can therefore be considered as:

$(n_e - n_o) > 0$ (i.e. positive)

The state of polarization of the radiation 65B transmitted through the second crystal 62 therefore follows the sequence of polarization shown in FIG. 3B.

However, in the case of the first crystal 61, then the crystal is rotated 90°, so that the optical axis $C_1$ lies parallel to the Y axis. In this case the effective birefringence is given by the difference:

$(n_e - n_o) < 0$ (i.e. negative)

Figure 6B:
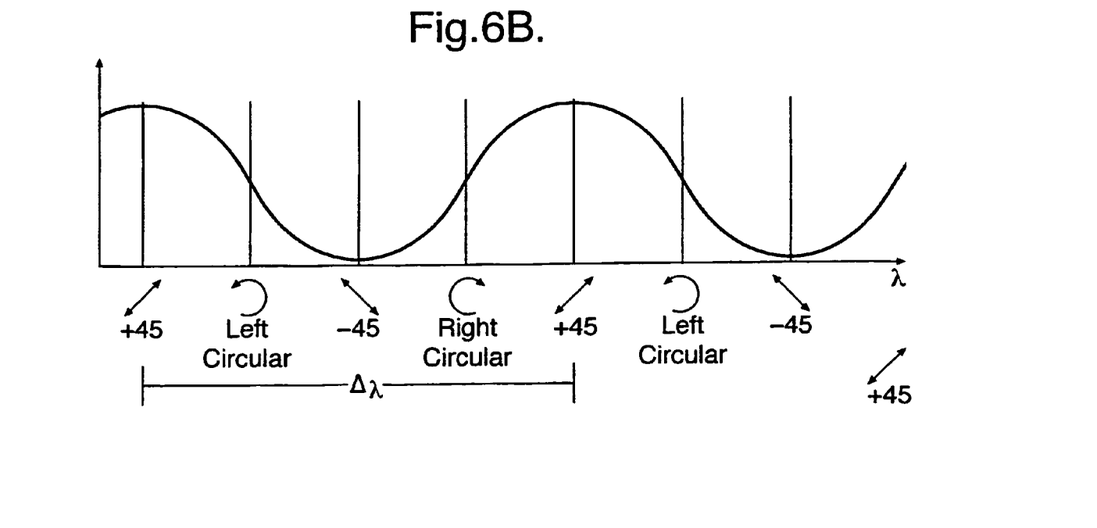
FIG. 6B shows the transmission spectrum for different wavelengths for the second crystal of the apparatus shown in FIG. 6A when no signal is applied to the induced birefringent member.

Accordingly, the state of the polarization of the radiation 65A follows the polarization sequence shown in FIG. 6B, which is effectively the reverse of the sequence shown in 3B. This is equivalent to the cIPF scanning in the opposite direction to the cIPF of FIG. 4B.

The radiation output from the first and second crystals is represented by the rays 66A,66B which pass through the induced birefringent member $S_{in}$. The induced birefringent member $S_{in}$ is driven by an appropriate sinusoidal driving signal as described with respect to FIGS. 4B,4C and 4D. This causes the polarization of the radiation to alter in accordance with the applied driving signal. However, because of the different alignment of the first and second crystals 61,62, the variation will be different for each portion of the radiation 66A,66B.

The radiation output from the induced birefringent member $S_{in}$ is then transmitted through the polarizer $P_2$ as shown. As a result of the different polarization states, the relative transmission intensities for each portion of the radiation 66A,66B will be different if the spectrum of absorption is asymmetrical and will be equal if the spectrum of absorption is symmetrical.

As described with respect to FIG. 4B, the cIPF can act as a modulator, scanning the vibrational-rotational spectrum of the sample gas from one maxima, to the next and back again. However, in this example, because the cIPF includes the orthogonally arranged first and second crystals 61,62, the cIPF acts as two modulators, with the modulators scanning in opposite directions in synchronization.

The first portion of the radiation 66A which passed through the crystal 61 and the second portion of the radiation 66B which passed through the crystal 62 are then detected by the detector 16, which effectively superposes the two sets of radiation.

If the individual absorption lines of the quasi periodic absorption spectrum of the target gas are not symmetrical, the sinusoidally varying intensity of the beam incident to the detector will not have a constant amplitude, but will be modulated because of the spectral asymmetry. This will also happen, if the detector sensitivity changes monotonically with the wavelength.

However, if the two transmission spectra moving in opposite directions are superposed, then the modulated intensities of each resulting signal cancel resulting in radiation of constant amplitude.

Figure 6C:
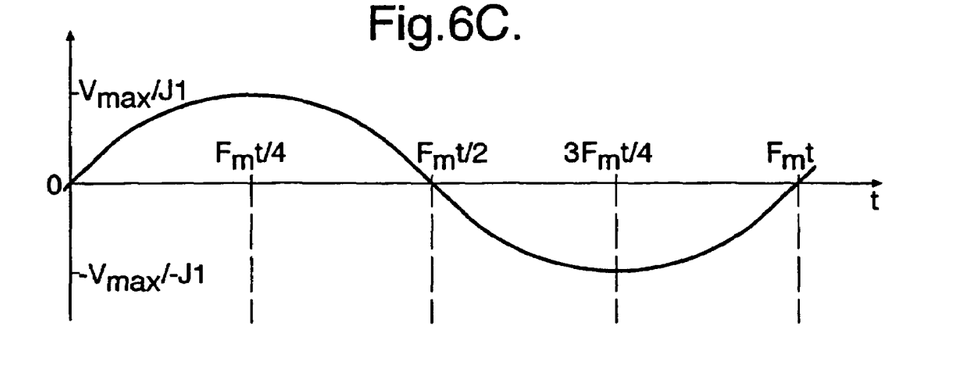
FIG. 6C shows the driver voltage applied to the apparatus of FIG. 6B against time with amplitude in which the induced birefringency is equal to half-wave phase plate or phase retardation II.
Figure 6D:
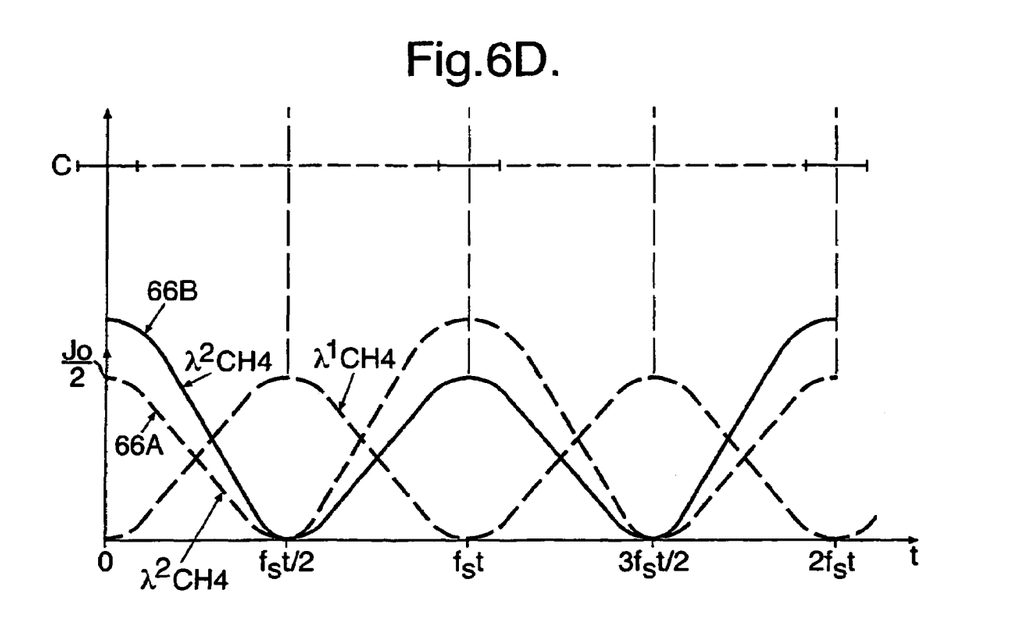
FIG. 6D shows the transmission amplitude intensity against time for the apparatus shown in FIG. 6B and for the driver voltage shown in FIG. 6C.
Figure 6E:
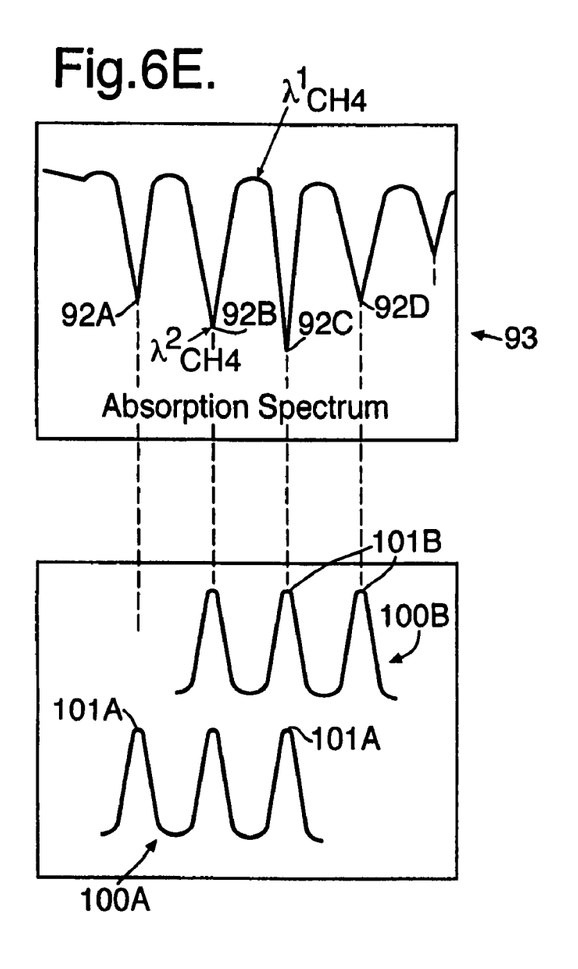
FIGS. 6E and 6F are examples of the transmission spectrum of the apparatus of FIG. 6B, compared to the absorption spectrum of methane, for the driver voltage shown in FIG. 6C.

This will now be described in more detail with respect to FIGS. 6C, 6D, 6E and 6F. In FIG. 6E, the transmission spectrum for the first portion of the radiation 66A and the second portion of the radiation 66B are shown by 100A and 100B respectively.

As shown, the transmission peaks 101A of the spectrum 100A are aligned with the absorption peaks 92A, 92B and 92C of the absorption spectrum 93 of the gas to be detected. Meanwhile, the transmission peaks 101B of the second filter 100B are aligned with the peaks 92B,92C,92D of the absorption spectrum 93. As the peak 92A is larger than the peak 92D, the amount of radiation transmitted by the first transmission filter 100A is less than that transmitted by the second filter 100B.

Accordingly, the intensity of the radiation 66A is lower than the intensity of the radiation 66B. This is shown in FIGS. 6C and 6D. In this case, the intensity of the radiation 66A and 66B at the wavelength $\lambda^2_{CH4}$ are as shown.

Figure 6F:
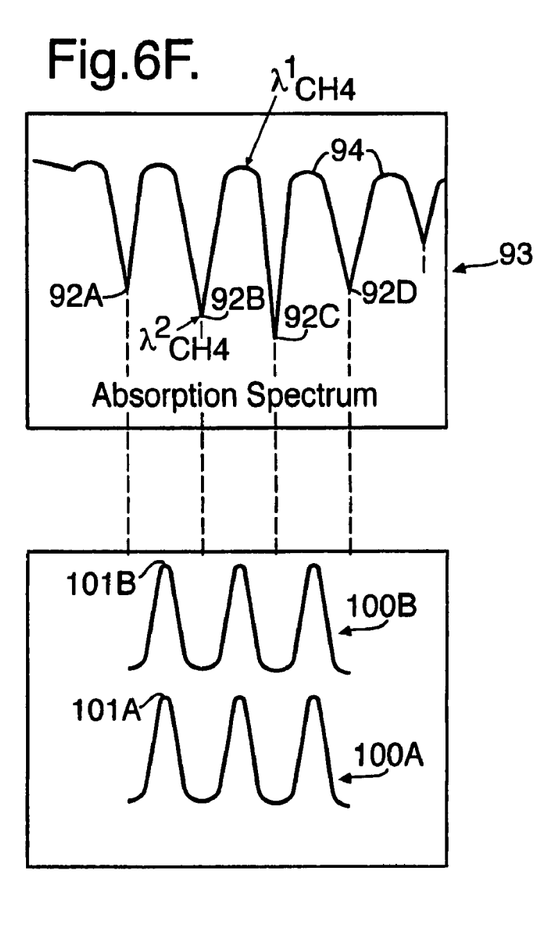

When the filter 100A scans to the right, the filter 100B scans to the left. Accordingly, because the filters 100A,100B are located at the same spectral position, as shown in FIG. 6F, the amount of radiation at the wavelength $\lambda^1_{CH4}$ transmitted by the filters 100A,100B is equal, as shown in FIG. 6D.

If only one of the portions of radiation 66A,66B were transmitted, then this would result in the intensity of radiation at wavelength $\lambda^2_{CH4}$ being detected varying with time. However, by superposing the two portions of radiation 66a,66B then the intensity of radiation detected at times $nF_sT$ will be constant. This means that the detector will detect a constant intensity of radiation for each wavelength $\lambda^1_{CH4}$, $\lambda^2_{CH4}$ at the appropriate detection time as indicated by the composite intensity (as shown in FIG. 6D).

This therefore overcomes the problem of asymmetries in the absorption spectrum of the detected substance. The problem of changes in detector sensitivity is solved in the same way.

An additional feature shown in the present example is the ability to shift the transmission spectrum by a small amount, by regulating the temperature of the first and second crystals 61,62 using the heating and/or cooling elements 63. This is possible because both the crystal's thickness and birefringence are temperature dependent. The possibility of using temperature adjustment as a means of fine tuning the exact location of the transmission maxima of the etalon results in lower manufacturing costs for the etalon crystal.

Figure 7A:
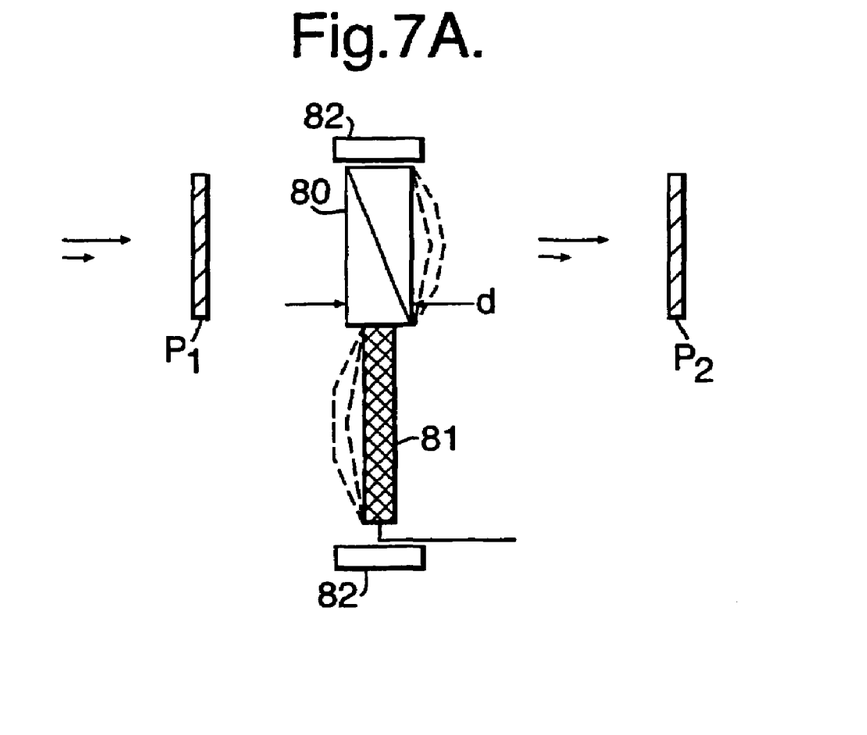
FIG. 7A is a schematic diagram showing apparatus according to the second aspect of the present invention.

An example of a cIPF in accordance with the fourth aspect of the present invention will now be described with reference to FIG. 7A. In this case the cIPF consists of an input polarizer $P_1$ and an output polarizer $P_2$. However, in this case the birefringence is produced by a single birefringent crystal 80 coupled to a piezoelectric driver element 81. The cIPF also includes temperature adjustment means, such as heating and/or cooling elements 82 which operate to maintain the crystal 80 at a constant temperature.

The crystal 80 is formed from a crystalline material that possesses both a natural birefringence, plus an induced birefringence, when the crystal is stressed. This may be any form of single axis crystalline material such as Crystalline Silicon, Islandic Spar, Tellurium Dioxide or the like. Accordingly, the resulting phase retardation that the crystal 80 causes is the sum of the individual retardations due to the natural birefringence and due to the induced birefringence. This therefore depends on both the mutual orientation of the optical axes of the crystals and the applied stress.

In use, when no stress is applied by the piezoelectric driver element 81, then the entire birefringence of the crystal 80 is due to the natural birefringence. However, when a driver signal is applied to the piezoelectric driver element 81, then a stress is applied to the crystal 80 causing an induced birefringence to be generated. As in the example of FIG. 4B, the driving signal, the crystal 80 and the piezoelectric driving element 81 are arranged to generate a standing wave along the length of the crystal 80.

This allows the birefringent crystal S and the induced birefringent member $S_{in}$ of the cIPF 15 shown in FIG. 5, to be replaced by a single crystal 80, coupled to piezoelectric driver element 81. The piezoelectric driver element 81 would be coupled to the voltage source 17, which provides the driver signal, in the normal way. Operation of the CIPS would then be achieved in the normal way, as described with respect to FIG. 5.

Furthermore, the cIPF can be tuned to shift the transmission spectrum by a small amount, by regulating the temperature of the crystal 80 using the heating and/or cooling elements 82. This is possible because both the crystal's thickness and birefringence are temperature dependent. As mentioned above, this allows the etalon to be fine tuned resulting in lower manufacturing costs for the etalon crystal.

Figure 7B:
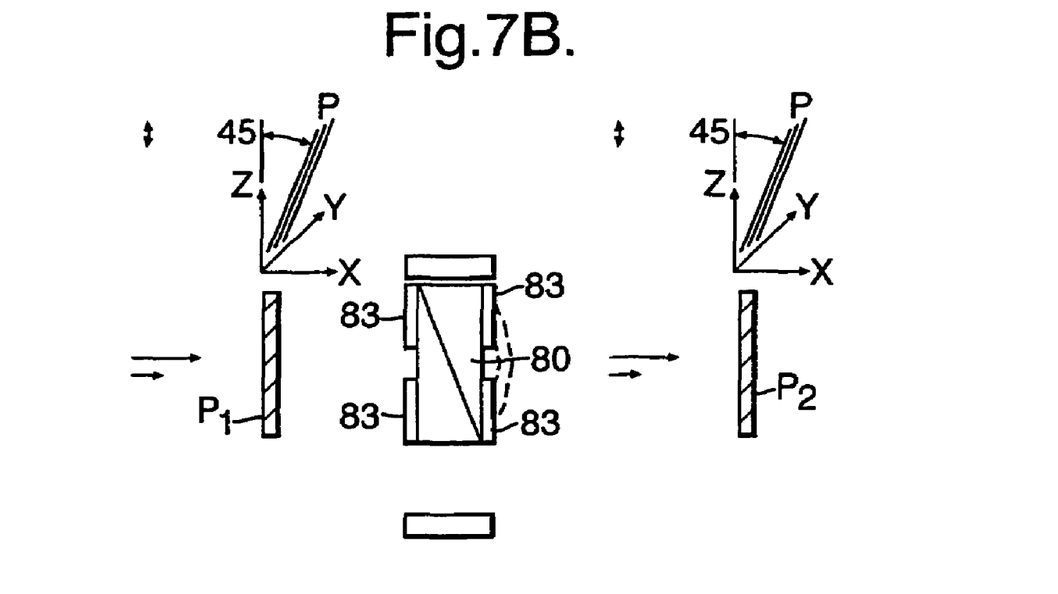
FIG. 7B is a schematic diagram showing a second example of apparatus according to the second aspect of the present invention.

A second example of a cIPF according to the fourth aspect of the present invention is shown in FIG. 7B. In this case, the crystal 80, which again is formed from a crystalline material having both a natural birefringence and an induced birefringence, has a number of electrodes 83 coupled thereto, instead of a piezoelectric driving element 81.

With no signal applied to the electrodes, the birefringence of the crystal 80 is due only to the natural birefringent component. However, when an appropriate driving signal is applied to the electrodes, this causes the electrodes to stress the crystal 80 so as to generate a standing wave along the length of the crystal 80. This causes the generation of the induced birefringence, so that the cIPF acts as a modulator, as required.

Again heating and/or cooling elements 82 operate to control the temperature of the crystal, allowing the transmission spectrum to be controlled.

This system can also therefore be used to replace the cIPF of FIG. 5, without effecting the operation of the CIPS.

Figure 8A:
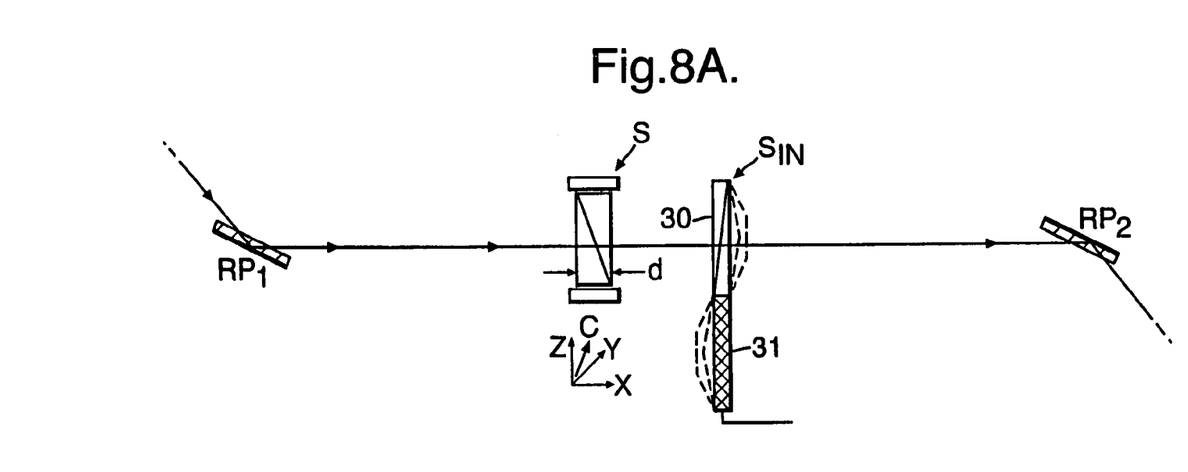
FIG. 8A is a schematic diagram of a first example of apparatus according to the third aspect of the present invention; and, FIG. 8B is a schematic diagram of a second example of apparatus according to the third aspect of the present invention.

FIG. 8A shows an example of a cIPF in accordance with a fifth aspect of the present invention. In this case, the apparatus consists of an input polarizer $RP_1$ and an output polarizer $RP_2$. Again, a birefringent crystal S and an induced birefringent member $S_{in}$ are utilized. In this example, the polarizers $RP_1$ and $RP_2$ are reflection polarizers. Accordingly, the radiation output from the polarizer lies in the plane defined by the incident beam and the edge of the polarizer.

For proper cIPF operation the plane of polarization of the beam incident to the cIPF section must therefore make an angle of 45° with respect to the birefringent crystal's optical axis whilst the optic axis of the crystal remains perpendicular to the direction of travel of the radiation.

In order to achieve this, the birefringent crystal S and the induced birefringent member $S_{in}$ are rotated by 45° around the direction of travel of the incoming radiation. This is indicated by the optic axis of the birefringent crystal S being aligned at 45° to the Z axis, as shown. The function of the cIPF 15 is then as previously described with respect to FIG. 4B. Accordingly, the cIPF can be used in the apparatus of FIG. 5.

Figure 8B:
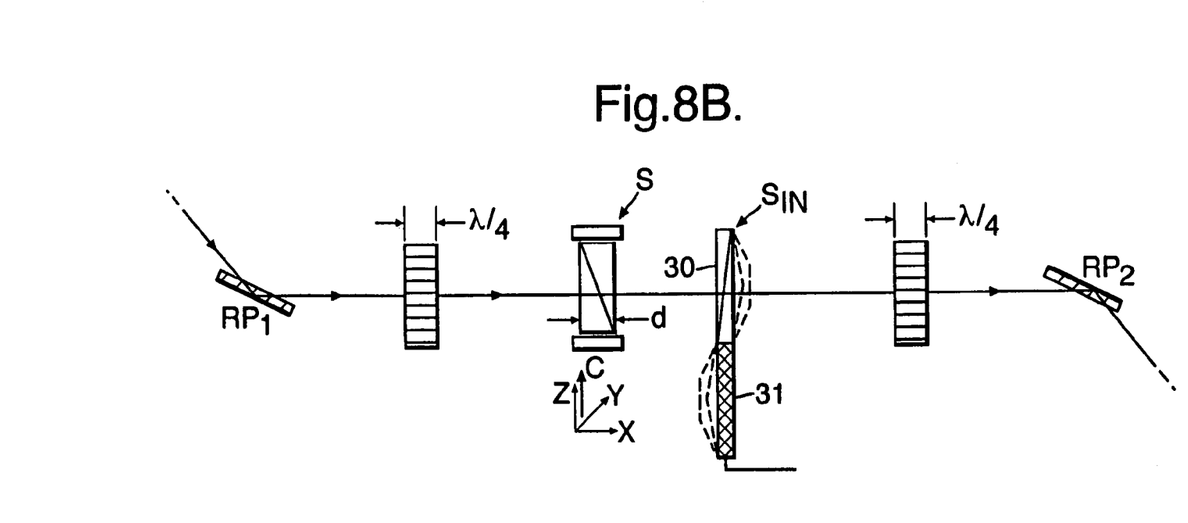

An alternative is to use the apparatus shown in FIG. 8B. In this case, the complexity of positioning the birefringent crystal S and the induced birefringent member $S_{in}$ with their respective optic axes positioned at 45° with respect to the vector of linear polarization of the incoming radiation can be avoided by using the additional first and second quarter wave retarders $Q_1, Q_2$ as shown.

In this case the birefringent crystal S and the induced birefringent member $S_{in}$ are positioned with the optical axis perpendicular to the direction of travel of the incident radiation but at any angle with respect to the vector of polarization of the light reflected from the first polarizer $RP_1$.

As in the apparatus of FIG. 8A, the radiation reflected from the input polarizer $RP_1$ is polarized in the plane defined by the incident beam and the edge of the polarizer $RP_1$. However the quarter wave retarder $Q_1$ modifies the radiation so that it is circularly polarized. The circularly polarized radiation is then incident on the birefringent crystal S.

Using circularly polarized radiation allows the direction of polarization of the reflective polarizers to be arbitrary irrespective of the orientation of the optical axis of the etalon. Consequently, one can rotate the direction of the polarizer (and quarter wave retarder) arbitrarily without changing the status of its circular polarization (if it was originally CW polarized it will still be CW polarized after rotation). As an example, the polarization of sun radiation scattered by the atmosphere depends on the angle between the sun and the horizon. A passive CIPS can have its polarizers rotated to optimize at any time the intensity of radiation reaching the instrument's collimator.

These modify the polarization of the incident radiation in a similar manner to when linearly polarized radiation is used. The radiation output from the induced birefringent member $S_{in}$ is then modified by second quarter wave retarder $Q_2$ and then reflected from the output polarizer $RP_2$.

In this case the role linearly polarized beams exiting the cIPF section at the absorption maxima and minima is replaced by circularly polarized beams oriented clockwise for the absorption maxima and counter clockwise for the minima. Again, apart from the above, the functionality is as previously described with respect to FIG. 4B.

It will be realized that the use of a single crystal to replace the birefringent crystal S and the induced birefringent members $S_{in}$ could be implemented in the examples shown in FIGS. 6, 8A and 8B. Furthermore, the use of the first and second portions of radiation shown in FIG. 6 could be implemented in the examples shown in FIGS. 7A, 7B, 8A, and 8B.

The invention claimed is:

1. A filter for use in a spectrometer, the filter being arranged to filter radiation transmitted by a sample, the filter comprising:
   a first polarizer for polarizing the radiation transmitted by the sample;
   a birefringent element responsive to an applied signal, wherein the birefringent element modifies the polarization of the polarized radiation in accordance with the wavelength of the radiation and the applied signal; and,
   a second polarizer for polarizing the radiation transmitted by the birefringent element, the radiation being transmitted in a transmission direction, characterized in that the birefringent element comprises:
   a birefringent member having a first birefringence, the birefringent member being responsive to a force applied thereto to generate an additional second birefringence; and, a driver for applying a force to the birefringent member in accordance with the applied signal, and the driver comprises a piezoelectric member coupled to the birefringent member on one end or at two opposite ends.

2. A filter according to claim 1, wherein the birefringent member comprises a single axis crystalline material.

3. A filter according to claim 1, the birefringent member and the piezoelectric member being arranged such that the application of the signal to the piezoelectric member generates a standing wave along the combined length of the birefringent member and the piezoelectric member.

4. A filter according to claim 1, wherein the driver comprises a number of piezoelectric electrodes coupled to the surface of the birefringent member, the electrodes being arranged to generate a standing half-wave along the length of the birefringent member, in response to the applied signal.

5. A filter according to claim 3 or claim 4, wherein the standing wave is generated in a direction parallel to the direction of the optic axis of the birefringent member.

* * * * *